United States Patent [19]

Martin et al.

[11] Patent Number: 4,517,043
[45] Date of Patent: May 14, 1985

[54] CUSTOM DENTURE FABRICATION TECHNIC

[76] Inventors: Raymond H. Martin, 88 Brisbon Rd., Somerset, Mass. 02726; Ugo S. Garganese, 1790 Warwick Ave., Warwick, R.I. 02889; John R. Griffin, 5 Franconia St., Dorchester, Mass. 02122

[21] Appl. No.: 536,363

[22] Filed: Sep. 26, 1983

Related U.S. Application Data

[63] Continuation-in-part of Ser. No. 271,806, Jun. 8, 1981, abandoned, and Ser. No. 405,427, Aug. 5, 1982, Pat. No. 4,500,289, and Ser. No. 71,948, Sep. 4, 1979, Pat. No. 4,337,039.

[51] Int. Cl.³ .................. B29C 27/00; B29C 17/03; B29C 17/10; B29C 23/00
[52] U.S. Cl. ....................... 156/196; 264/17; 264/522; 264/138
[58] Field of Search ............ 156/196, 212, 245, 286; 264/17, 522, 138, 500

[56] References Cited

U.S. PATENT DOCUMENTS

| | | | |
|---|---|---|---|
| 514,201 | 2/1894 | Robertson | 264/17 |
| 731,674 | 6/1903 | Finnell | 264/17 |
| 2,101,431 | 12/1937 | Groff | 264/17 |
| 2,341,604 | 2/1944 | Dresch | 264/17 |
| 2,539,773 | 1/1951 | Fournet | 264/17 |
| 2,551,812 | 5/1951 | Nelson | 264/17 |
| 2,551,932 | 5/1951 | Dimmer | 264/17 |
| 2,682,084 | 6/1954 | Anchors | 264/17 |

Primary Examiner—Willard E. Hoag

[57] ABSTRACT

A method of fabricating a custom denture using a preformed tooth arch and a custom formed denture base, attaching these units with a self polymerizing plastic, using a plasterless keying articulator in conjuction with an occlusal translator thereby completing the entire fabrication of a custom denture on the articulator without the conventional waxup, flasking, processing which is the present state of the art.

5 Claims, 17 Drawing Figures

CUSTOM DENTURE FABRICATION TECHNIC

This application is a continuation-in-part of application Ser. No. 06/271,806 filed 06/08/81 and now abandoned and also a continuation-in-part of application Ser. No. 06/405,427 filed 08/05/82 now U.S. Pat. No. 4,500,289 and Ser. No. 06/071,948 filed 09/04/79 now U.S. Pat. No. 4,337,039.

The above mentioned applications are incorporated herein by this reference.

BACKGROUND OF THE INVENTION

While denture forming technics and processing methods are known, none to our knowledge have a complete system to fabricate a custom denture which eliminates the materials, time and skill that this technic does.

In 1939 the Dupont Company and the Rohm and Haas Company marketed a methylmethacrylate and called it lucite, the forrunner of acrylic resins today. The material was made in powder form and a liquid of the same composition added for mixing. The two items used in the right proportion and correct manipulation was injected into a mold which contained artificial teeth and cured into some of several curing technics of applying time and temperature of several hours to produce a hardened base which would have artificial teeth attached. In 1948 a slight change in the monomer system brought about a self-curing material. The acrylic resin is used all over the world today and with only slight changes and improvements since the original conception. The improvements are pour type, soft liners and cross linked acrylic resin.

The usual process of fabricating a prosthesis commences when a dentist takes impressions of the patient's edentulous maxillary and mandibular arches. These impressions are negative imprints of the arches and become the moulds into which the gypsum material for the positive dental cast is poured. These positive casts are duplicates of the patient's arches and become the primary model to which the prosthesis is to be constructed.

In order to construct a prosthesis these dental casts are normally mounted in a dental articulator in order that the maxillary and mandibular casts are maintained in the same anatomical relationship as in the mouth of the patient. Another reason why the dental casts are mounted in the articulator is to permit the arrangement of the individual denture (false) teeth into their proper position for occlusion. These individual denture teeth are set in wax. On the master cast or model, wax is placed to provide for proper thickness for the denture base and refined by carving to conform to the patient's mouth. This completely waxed denture and cast is then invested in one-half of a metal denture flask with plaster. After this is hardened a separator is applied. The second half of the flask is then filled with plaster. This mix is also allowed to harden. The completed flask is then submersed in boiling water and after sufficient time the two halves of the flask are separated. The remaining wax is removed and the mold is meticulously cleaned with soap and boiling water.

A coating is applied to the mold to shield the acrylic resin from the moisture in the plaster. A proper mix of acrylic resin is made and placed in the mold and by means of pressure is trial packed until sufficient acrylic resin is contained in the mold, this could take several trials.

These flasks under pressure are placed into a curing unit for up to 12 hours depending on manufacturer's specifications. After a cooling period the mold is removed from the metal flask, the hardened plaster is carefully cut to allow removal of the cured denture. The master cast is then removed from the denture. The excess hardened acrylic resin is then removed and polished.

SUMMARY OF THE INVENTION

The principle object is to provide a custom denture without going through the various and time consuming steps necessary in the present state of the art, such as setting of teeth individually in wax on an articulator, custom forming the wax, flasking, boiling and eliminating the wax from the flask, mixing acrylic, packing, curing, removal of processed denture from the flask, finishing and polishing. The object of this invention is to fabricate a custom denture completely from start to finish on an articulator.

The dentist provides an upper and lower impression of the patient's jaws, a wax centric and vertical relation registration and a millimeter measurement of the distance between the anterior papilla and the upper lip at rest.

The impressions are now ready for the new method of making the casts, rather than the procedure presently used in the state of the art, differing in that a ferromagnetic metal keying disc with a square hole and lanced at the edges, is placed over a flexible model base former that has a square nipple the same size as the keying disc. The flexible model former also has the wall around its edge to control the base thickness which is part of the aforementioned U.S. Pat. No. 4,337,039, is used in this first step by the technician by making a mix of artificial stone in the usual manner and vibrates the soft mix into the impressions; he then fills the model base former with the artificial stone mix and turns the soft stone filled impressions onto it; when the artificial stone has hardened it is removed from the model former and trimmed leaving an upper and lower cast of the patient's jaws with a keying metal disc and square hole in its base. The casts now have a uniform base formed by the flexible former, a square keying disc in its base with a square hole into the cast base which will fit onto the plasterless articulator of U.S. Pat. No. 4,337,039 and also fitted over a vacuum machine having a square metal protruding nipple in its vacuum center the same dimensions as the keying square hole.

The wax registration impression provided by the dentist is luted to the upper and lower casts and placed on the plasterless articulator, U.S. Pat. No. 4,337,039, by placing the lower cast on the lower member of the articulator over the square nipple and secured by the magnet, the upper assembly is loosened to accomodate the bite registration by moving the upper square nipple into the upper cast, secured by magnet, and adjusting the upper ball joint and slide bar to the position of the bite registration and then locking the ball joint and slide bar by tightening the wing nuts of the upper assembly, the rear verticle pin is now set to the bite registration and locked with the set screw. The plasterless articulator is now keyed to the patient's measurements.

The bite block and upper and lower casts are now removed, the upper plasterless articulator assembly is removed temporarily, being replaced with a second upper articulator assembly. A denture occlusal mounting translator, a of application and Ser. No. 06/405,427, a tool for the plasterless articulator of Pat. No. 4,337,039, this tool will transfer the patient's occlusal measurement. This translator has a keying square hole in its base that matches the square nut of the lower assembly of the articulator which mounts thereto; it also has a rear adjustable horizontal bar, a zero degree table, and an anterior papilla meter reader which elevates to a given measurement in which it also has a pointer on one end and an adjustable cast holder on the opposite end. The denture occlusal mounting translator is placed over the square protruding nut of the lower assembly of the plasterless articulator and held in place by the magnet of the lower assembly of the plasterless articulator.

The upper cast is placed on the horizontal bar of the translator at the hammular notches of the cast, which levels the cast to the correct plane of the patient's occlusal measurement, the bar is then raised by loosening the rear set screw to bring the cast two millimeters above the horizontal zero degree translator table which will allow the custom denture base to have the necessary space for construction of the custome denture base, the screws are now locked in this position.

The anterior papilla elevator is now loosened and set to the papilla reading of the patient as supplied by the dentist at the time of the bite registration. The cast now lies on the horizontal rear bar and the papilla elevator in its correct position, and the anterior papilla meter reader is now locked by the front screw, the cast is now above the zero degree table of the translator exactly where all measurements correspond.

The second upper plasterless articulator assembly is now loosened at the slide bar and ball joint and the square nut with the upper magnet is placed into the cast and the upper ball joint and slide bar are now locked, locking the cast. The papilla reader is now turned with the pointer indicating the center of the anterior papilla and lowered to the top of the zero degree table of the translator, indicating the center of the patient's central teeth, and locked with the front screw. The horizontal bar at the rear of the zero degree table is unlocked and removed to allow for easy access.

The upper cast is now removed from the upper plasterless articulator assembly, and placed over a square metal protrusion in the center of the vacuum machine, this allows the vacuum to penitrate deep inside the cast, which is a further improvement over the state of the art being used, this method increases the custom fit to the cast for accuracy.

The plastic blank is placed in the holder of the vacuum machine above the cast and under the heating unit which will soften the plastic blanks, once this is done it is lowered over the cast and locked, at which point the vacuum pulls the softened plastic blank and forms the custom denture base, and it is allowed to cool.

The cast is then released from the machine and the custom denture base remains on the cast, and the plastic denture base is trimmed around its peripheral border to remove the excess, it is now returned to the plasterless articulator which returns the cast and custom denture base to the correct distance between the articulated cast with the custom denture base intact, and the zero degree table and it is now ready for the attachment of the arch which consists of teeth preset to a plastic contured ridge with the interproximals finished needing no finishing around the teeth, the selection is made from three arches: small, medium and large, with the teeth preset, that will be selected from the indication of measurement of the patient's maxillary and mandibular ridge, the attachment of the arch with the teeth, takes place on the plasterless articulator.

Placing the arch with the preset teeth to conform to the dentist's original measurements of the patient's jaws and already transferred to the denture occlusal mounting translator patent pending of application Ser. No. 06/405,427, the arch with preset teeth is placed on the translator zero degree table and with the center indicator of the translator table the arch with the preset teeth is attached to the custom denture base.

The upper cast with the upper denture still on the cast is removed from the denture translator table of application Ser. No. 06/405,427, and the upper plasterless articulator assembly. The translator table is now removed from the lower member of the plasterless articulator, and the first original upper plasterless articulator assembly is placed back onto the articulator, which re-establishes the measurement of the patient.

The upper cast with the denture is placed back onto the original upper assembly as it will key back onto the preset position.

The lower cast is now placed over the square protrusion of the vacuum machine, the plastic blank is placed into the holder above the model and under the heating unit of the vacuum machine and softened to a pliable state and at this point the rimmed holder with the softened plastic blank is pressed over the cast and the vacuum pressure draws the plastic blank into position, the vacuum also drawing through the internal part of the cast from the square protrusion of the vacuum machine into the cast, which is an improvement over the present state of the art method being used.

The plastic custom denture is now allowed to cool and once cooled, removed from the vacuum denture base is trimmed around the peripheral border, and the cast with the custom denture base is placed back onto the lower assembly of the plasterless articulator, which is now in its original keyed position corresponding to the patient's bite.

A lower arch with teeth preset that articulate with the upper denture is now placed over the lower custom denture base and brought into articulation with the upper denture that is already on the upper assembly of the plasterless articulator, and the lower arch with its preset teeth is attached to the lower custom denture base which now completes the upper and lower dentures, both dentures are now removed from the plasterless articulator and polished around the peripheral border in the usual state of the art manner to final completion.

The single denture is done in the same manner, except the patients cast of natural teeth, supplied from an impression taken by the dentist, and poured in the same manner as aforementioned, into the flexible model former with the keying disc, which cast is used against the edentulous cast. As used hereinafter, "impression" shall be understood to mean an impression of the edentulous gum or an impression of the patient's natural teeth where a single denture in contemplated.

BRIEF DESCRIPTION OF THE DRAWINGS

FIG. (1) shows impressions of patients upper and lower jaw which are negative imprints of the arches.

FIG. (2) shows key square hole metal disc

Figure 1:
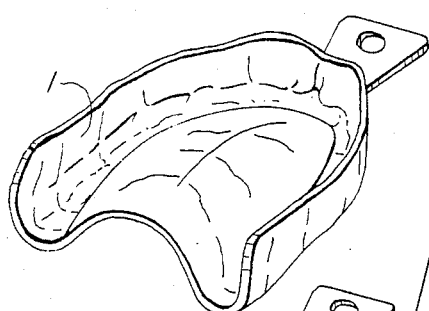
Figure 2:
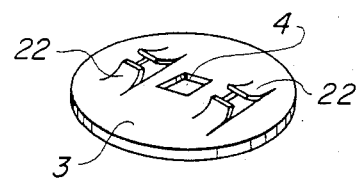
Figure 3:
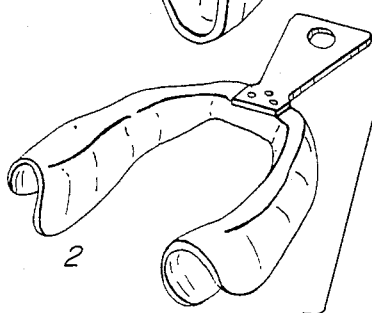
Figure 4:
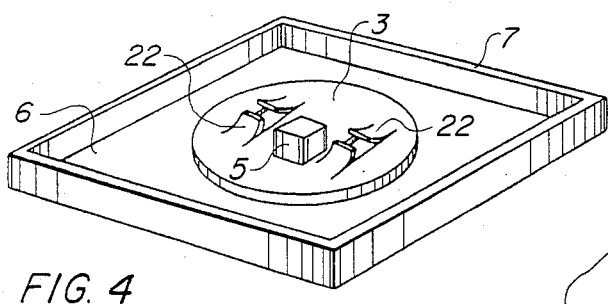
Figure 5:
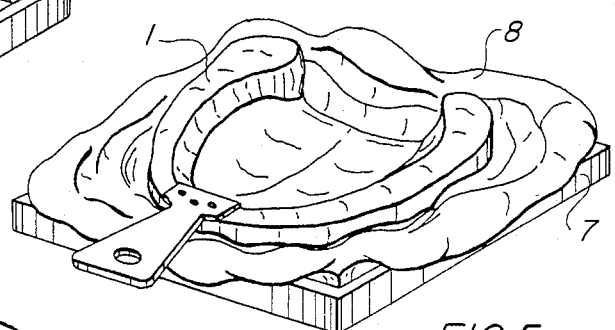
Figure 6:
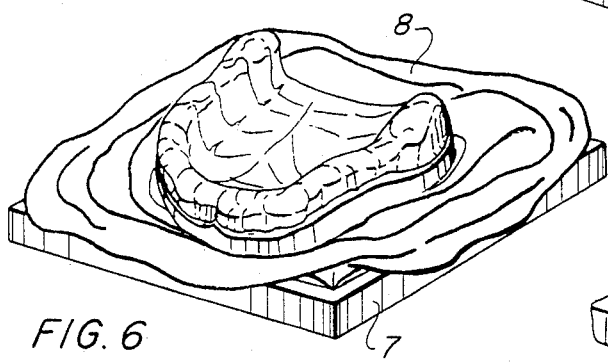
Figure 7:
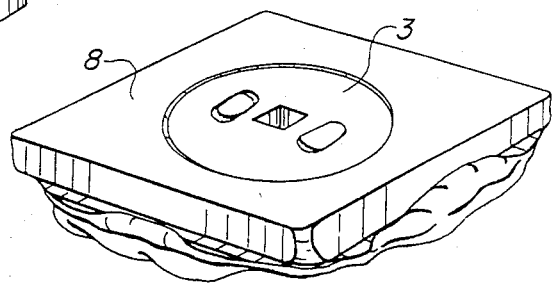
Figure 8:
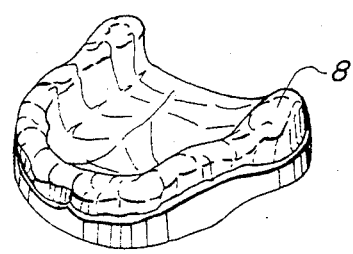
Figure 9:
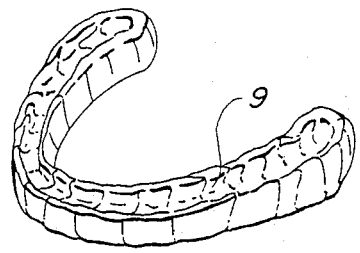
Figure 10:
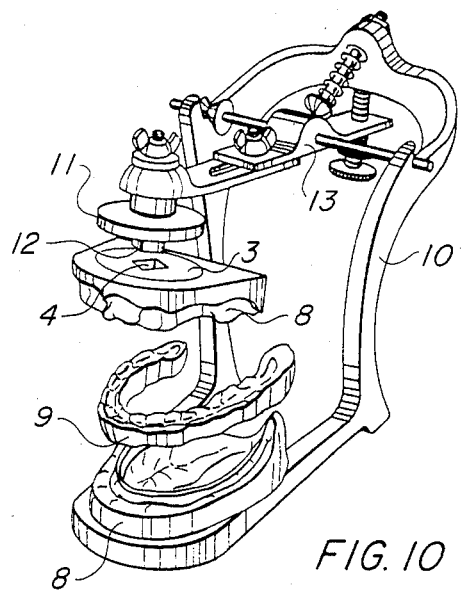
Figure 11:
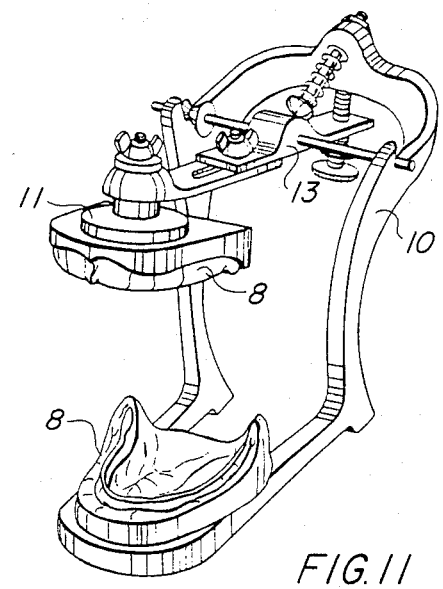
Figure 12:
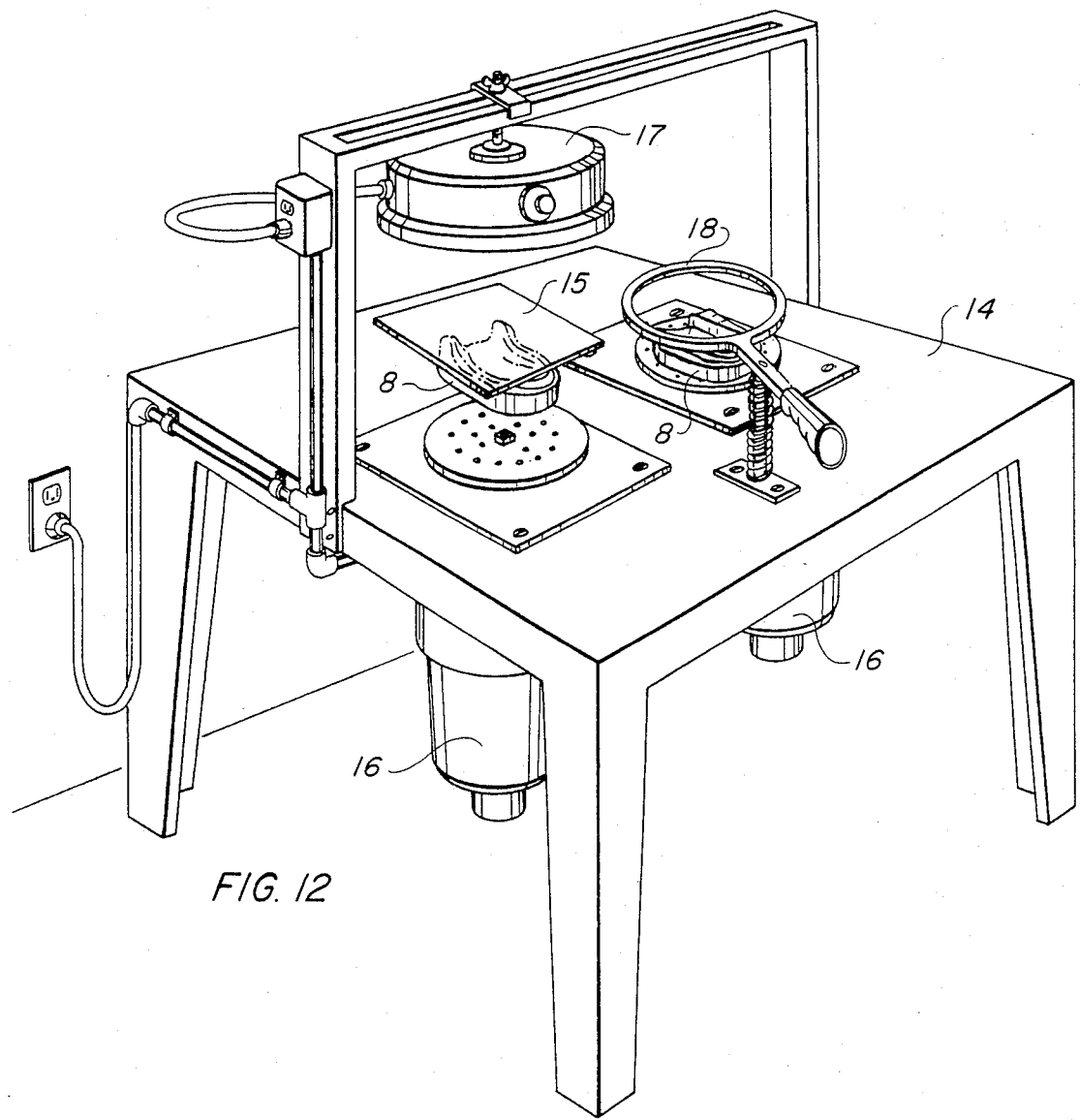
Figure 13:
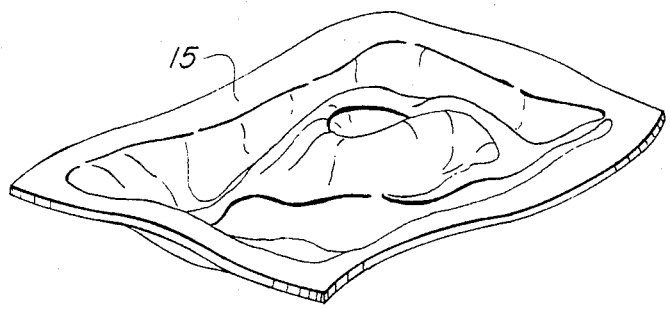
Figure 14:
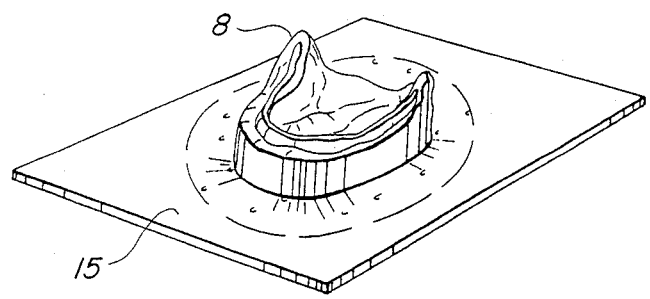
Figure 15:
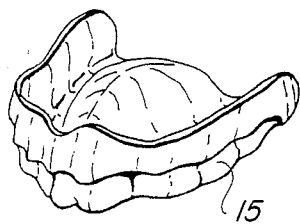
Figure 16:
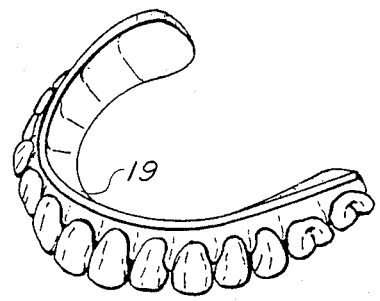
Figure 17:
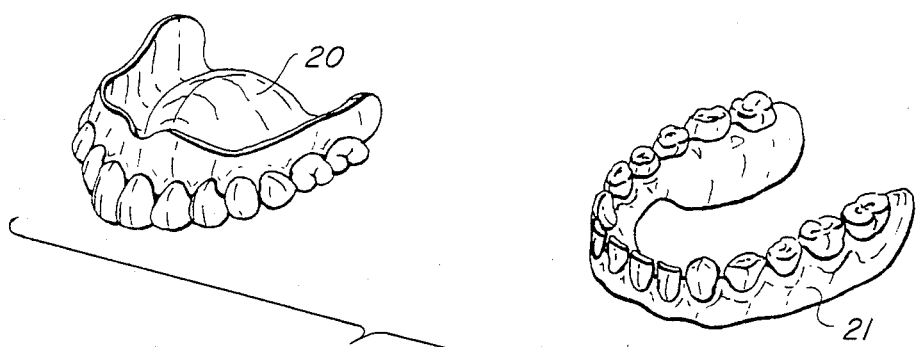

FIG. (3) rubber mold former with square nipple to receive metal disc.

FIG. (4) shows square hold disc in place over square rubber nipple ready to accept gypsum to lock disc to models.

FIG. (5) shows poured impressions which will lock discs into models.

FIG. (6) shows model after impressions which will lock discs into models.

FIG. (7) shows base of models showing disc lock in with preformed square hole in model which will be used to attach to plasterless articulator FIG. (8) shows model after being trimmed to perpheral roll.

FIG. (9) shows bite registration

FIG. (10) shows models placed into patients bite registration with lower model placed over square nut magnetized cap.

FIG. (11) shows the completion of articulation with the discs and bolts locked to patients measurements and bite registration.

FIG. (12) shows vacuum machine with a patients model over vacuum area.

A. shows acrylic blank over model
B. shows heat unit over acrylic blank
C. shows vacuum pumps
D. shows forming ring FIG. (13) shows heated acrylic blank losing memory before being drawn by vacuum to adapt to patients model.

FIG. (14) shows acrylic base now fully adapted to patients model

FIG. (15) shows molded denture base ready to receive tooth arch

FIG. (16) shows selected preformed tooth arch.

FIG. (17) shows the finished dentures on which the tooth arches have been cemented to the base and contured with self curing acrylic and polished ready for insertion

DESCRIPTION OF THE PREFERRED EMBODIMENTS

Step #1 a conventional impression FIG. (1) and bite registration FIG. (9) is taken of the upper and lower jaw Step #2 place key lock, square hole metal disc FIG. (2) over square nipple on rubber model former FIG. (3)

Step #3 make a gypsum mix in the conventional manner and vibrate into both impressions FIG. (1) fill rubber formers FIG. (4) place poured impressions over center of square former in the same operation FIG. (5) after material has set remove rubber former FIG. (3) and trim excess FIG. (8).

Step #4 lute patients bite registration FIG. (9) to models and attach to articulator which has a squared nut and magnet, FIG. (10) the square metal disc FIG. (2) in the base of model FIG. (7) will fit over the square nut and the metal disc will engage magnet on the articulator FIG. (10). Lock all adjustments on articulator and remove the patients bite registration FIG. (11).

Step #5 remove the models from articulator and place models on vacuum table FIG. (12) and place a suitable denture base material or acrylic sheet, on model FIG. (12A) allowing it to release all prior memory, FIG. (13) and become sufficiently pliable to be drawn by vacuum, FIG. (12C) giving an accurate form to the model of the jaw FIG. (14). Allow the acrylic base to cool and cut excess away to peripheral roll. The model with the acrylic base FIG. (15) is now ready to remount to articulator base, to keyed position FIG. (11). A self-curing base material may be used which would require vacuuming only.

Step #6 select preformed tooth arch of desired size and shade FIG. (16) and place it on the acrylic base by means of an acrylic cement to conform with patients mouth measurements as indicated by bite registration FIG. (10). Fill in area between tooth arch and acrylic base to desired contour with self-cure acrylic. Remove dentures from models, polish and they are ready to insert into the patient's mouth FIG. (17).

We claim:

1. A method for forming dentures from stock preformed dental arches having teeth pre-mounted thereon, and custom-made dental bases, comprising: forming cast stone jaw models against jaw impressions in suitable molds; removing the material of said impressions leaving the jaw molds; luting a wax bite registration impression between said jaw models to form an assembly; positioning said assembly on an articulator with said models keyed to the articulator in reproducible positions; removing the models from the articulator and heating and vacuum forming thermoformable plastic sheet material about said models and cooling said sheet material to form custom fitted denture bases; and returning the denture bases to said models; positioning said models in the same position on the articulator as before; attaching a suitable preformed plastics dental arch with preset teeth to each of said bases on said articulator to form said dentures.

2. The method of claim 1 wherein during the step of forming each of the cast stone jaw models, a magnetic disc having an aperture other than circular for mating with a corresponding nipple of a mold defined by a flexible member having upstanding peripheral walls is disposed in said mold with said nipple mating with said aperture and hardenable artificial stone mix is deposited in said mold over said magnetic disc and about projecting means on said disc to interlock said disc with said mix.

3. The method of claim 2 wherein the models are positioned in said reproducible positions on said articulator by said apertures mating with corresponding means on the articulator.

4. The method of claim 1 including trimming excess material from the vacuum formed sheet material to form said dental bases.

5. The method of claim 1 wherein fabricating a custom denture by means of mounting a dental cast on a translator having an elevating posterior horizontal bar and an elevating anterior papilla support arm and pointer attached thereto; also part of a zero degree table; engaging the dental cast at the hamular notches on the horizontal elevating bar above the zero degree table and elevating clearance between the tuberocities and zero degree table and the anterior papilla of the dental cast to the measurement of the patients papilla to lip line; and securing the dental cast in the desired position to the articulator, then removing the dental cast from the keyed position and fabricating a custom denture base and returning the cast with the custom denture base back to original keyed position on the articulator; then placing a preformed pink acrylic dental arch with a plurality of teeth and pink interproximals on the zero degree table, using the pointer of the translator to indicate the prepositioned center line and hold the arch and attaching said arch to the custom denture base entirely on a keyed articulator in conjunction with a dental occlusal translator.

* * * * *